US00PP25309P2

(12) United States Plant Patent
Westhoff

(10) Patent No.: US PP25,309 P2
(45) Date of Patent: Feb. 24, 2015

(54) ***PETUNIA* PLANT NAMED 'BALPERIME'**

(50) Latin Name: *Petunia×hybrida*
Varietal Denomination: Balperime

(71) Applicant: Ball Horticultural Company, West Chicago, IL (US)

(72) Inventor: Heinrich Westhoff, Südlohn (DE)

(73) Assignee: Ball Horticultural Company, West Chicago, IL (US)

( * ) Notice: Subject to any disclaimer, the term of this patent is extended or adjusted under 35 U.S.C. 154(b) by 182 days.

(21) Appl. No.: 13/815,592

(22) Filed: Mar. 12, 2013

(51) Int. Cl.
*A01H 5/00* (2006.01)

(52) U.S. Cl.
USPC ..... Plt./356.13

(58) Field of Classification Search
USPC ..... Plt./356.13
See application file for complete search history.

*Primary Examiner* — Anne Grunberg
(74) *Attorney, Agent, or Firm* — Audrey Charles

(57) ABSTRACT

A new and distinct cultivar of *Petunia* plant named 'Balperime', characterized by its purple with white-margined bicolored flowers, medium green-colored foliage, and moderately vigorous, trailing growth habit, is disclosed.

1 Drawing Sheet

Latin name of genus and species of plant claimed: *Petunia× hybrida.*

Variety denomination: 'Balperime'.

BACKGROUND OF THE INVENTION

The present invention relates to a new and distinct cultivar of *Petunia* plant botanically known as *Petunia×hybrida* and hereinafter referred to by the cultivar name 'Balperime'.

The new cultivar originated in a controlled breeding program in Südlohn, Germany. The objective of the breeding program was the development of with single type flowers, unique flower coloration, and trailing growth habit.

The new *Petunia* cultivar is a naturally-occurring sport of the proprietary *Petunia×hybrida* breeding selection coded 04K102063-054, not patented, characterized by its purple with white-margined bicolored flowers, light green-colored foliage, and a vigorous, trailing growth habit. The new cultivar was discovered as a side shoot and selected during September 2010 in a controlled environment in Südlohn, Germany.

Asexual reproduction of the new cultivar by terminal stem cuttings since September 2010 in Südlohn, Germany and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balperime' as a new and distinct cultivar of *Petunia* plant:

1. Purple with white-margined bicolored flowers;
2. Medium green-colored foliage; and
3. Moderately vigorous, trailing growth habit.

Plants of the new cultivar differ from plants of the parent primarily in having larger-sized flowers, darker colored foliage, and a less vigorous growth habit.

Of the many commercially available *Petunia* cultivars, the most similar in comparison to the new cultivar is 'Balperblues', U.S. Plant Pat. No. 21,493. However, in comparison, plants of the new cultivar differ from plants of 'Balperblues' in at least the following characteristics:

1. Plants of the new cultivar have a petal color different from plants of 'Balperblues'; and
2. Plants of the new cultivar have smaller flowers, as measured by corolla diameter, than plants of 'Balperblues'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balperime'. The plants were grown in 4.5-inch pots for 8 weeks in a greenhouse in West Chicago, Ill.

DETAILED BOTANICAL DESCRIPTION

Figure 1:
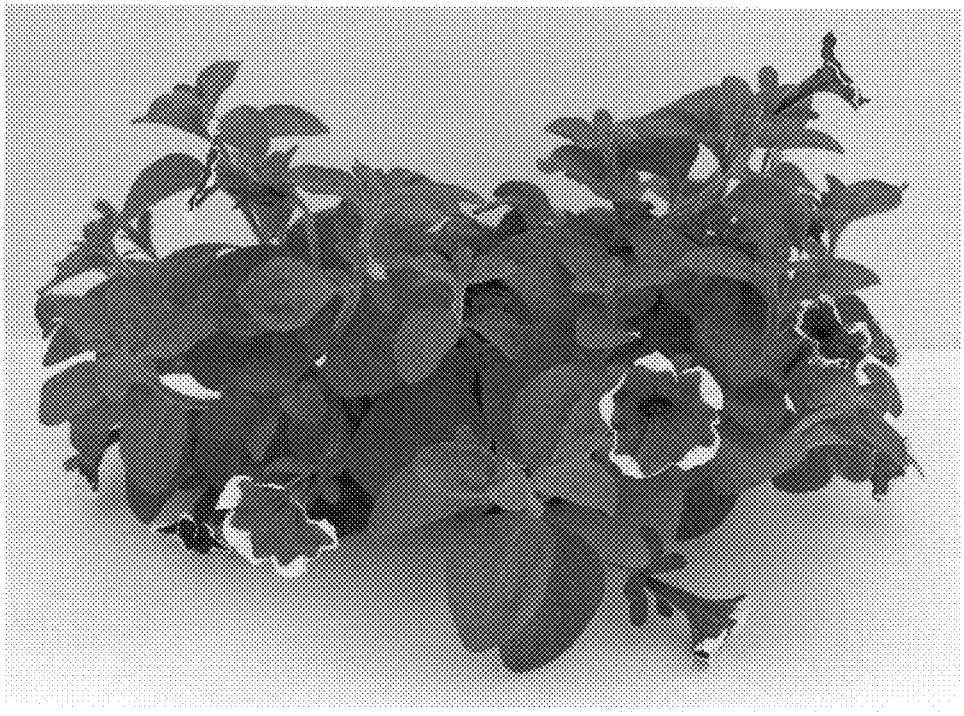
FIG. 1 illustrates a side view of the overall growth and flowering habit of 'Balperime'.
Figure 2:
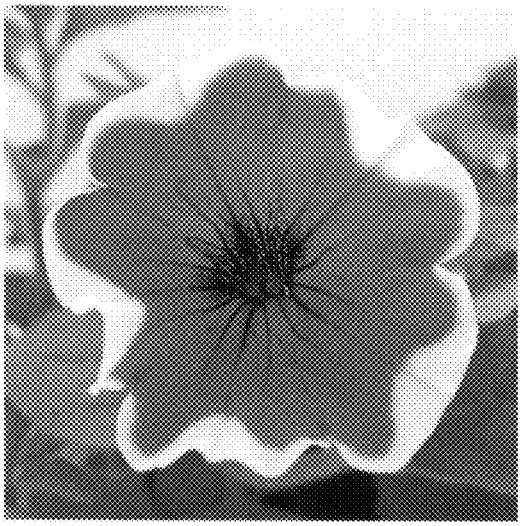
FIG. 2 illustrates a close-up view of an individual flower of 'Balperime'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in December 2012 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Petunia×hybrida* cultivar Balperime.

Parentage:

*Parent*.—Proprietary *Petunia×hybrida* breeding selection coded 04K102063-054, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Moderately vigorous, trailing habit.

*Size*.—Height from soil level to top of plant plane: Approximately 11.5 cm. Width: Approximately 35.5 cm.

*Branching habit*.—Freely branching, pinching improves basal branching. Quantity of main branches per plant: Approximately 5.

*Branch*.—Strength: Moderate. Length: Approximately 18.5 cm. Diameter: Approximately 3.0 mm. Length of central internode: Approximately 1.8 cm. Texture: Densely glandular pubescent with a mixture of long and short length hairs. Gland color: Colorless. Color of young and mature stems: 144A.

Foliage description:

*General description*.—Quantity of leaves per main branch: Approximately 14. Fragrance: Slight. Form: Simple. Arrangement on flowering stem: Alternate.

*Leaves*.—Aspect: Perpendicular to acute angle to stem. Shape: Ovate to elliptic. Margin: Entire. Apex: Broadly acute. Base: Attenuate. Venation pattern: Pinnate. Length of mature leaf: Approximately 5.1 cm. Width of mature leaf: Approximately 4.0 cm. Texture of upper and lower surfaces: Moderately glandular pubescent. Gland color: Colorless. Color of upper surface of young foliage: 137C with venation of 144B. Color of lower surface of young and mature foliage: Closest to 138B with venation of 144B. Color of upper surface of mature foliage: Closest to 137A with venation of 144B.

*Petiole*.—Length: Approximately 1.0 cm. Width: Approximately 2.0 mm. Texture: Densely glandular pubescent with a mixture of long and short length hairs. Gland color: Colorless. Color: 144B.

Flowering description:

*Flowering habit*.—'Balperime' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 8. Fragrance: Slight.

*Bud*.—Rate of opening: Generally takes 2 to 3 days for bud to progress from first color to fully open flower. Quantity per plant: Approximately 2.

*Bud just before opening*.—Shape: Oblong. Length: Approximately 4.0 cm. Diameter at apex: Approximately 7.0 mm. Diameter at base: Approximately 2.0 mm. Texture: Densely pubescent. Color of petals: N92D. Color of tube: N79A with venation of N79A.

*Corolla*.—Diameter: Approximately 4.2 cm.

*Petals*.—Quantity: 5, fused to form a tube. Shape: Obovate. Appearance: Velvety. Margin: Entire, slightly wavy. Apex: Rounded to slightly acute. Length from tube: Approximately 2.1 cm. Length of free portion: Approximately 7.0 mm. Width: Approximately 2.0 cm. Texture of upper surface: Glabrous. Texture of lower surface: Sparsely pubescent. Color of upper surface when first open: Closest to N81A with margins of NN155D and venation of N92C. Color of lower surface when first open: 86B with margins of NN155D and midveins of N79A. Color of upper surface when fully open: Closest to N78B with a faint overlay of N81A, margins of NN155D and venation of N79A. Color of lower surface when fully open: 86C with margins of NN155D and midveins of N79A.

*Corolla tube*.—Length: Approximately 2.5 cm. Diameter at distal end: Approximately 7.0 mm. Diameter at proximal end: Approximately 3.0 mm. Texture of inner surface: Glabrous. Texture of outer surface: Densely pubescent. Color of inner surface: 86B with venation of N92A. Color of outer surface: N79B with venation of N79A.

*Sepals*.—Quantity per flower: 5, fused at base. Shape: Ellipical. Apex: Acute. Length: Approximately 2.0 cm. Width: Approximately 7.0 mm. Texture of upper and lower surfaces: Densely glandular pubescent. Gland color: Colorless. Color of upper surface: 137A. Color of lower surface: 137C transitioning to 144A at base.

*Peduncle*.—Strength: Strong. Aspect: Acute angle to stem. Length: Approximately 4.8 cm. Diameter: Approximately 2.0 mm. Texture: Densely glandular pubescent with a mixture of long and short length hairs. Gland color: Colorless. Color: 144A.

*Reproductive organs*.—Androecium: Stamen quantity: 5, basifixed. Stamen length: Approximately 1.9 cm. Filament length of fixed portion: Approximately 8.0 mm. Filament color: 155D with an overlay of 86A. Anther shape: Bilobed. Anther length: Approximately 1.0 mm. Anther color: 85B. Pollen amount: Abundant. Pollen color: 85B. Gynoecium: Pistil quantity: 1 per flower. Pistil length: Approximately 2.5 cm. Stigma shape: Funnel. Stigma length: Approximately 2.0 mm. Stigma color: 145B. Style length: Approximately 2.0 cm. Style color: 145C with an overlay of N79A near stigma. Ovary length: Approximately 3.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balperime', substantially as herein illustrated and described.

* * * * *